(12) United States Patent
Leung et al.

(10) Patent No.: US 11,844,937 B2
(45) Date of Patent: Dec. 19, 2023

(54) SYSTEM AND METHOD FOR ADJUSTABLE LENGTH NEEDLE

(71) Applicant: CREDENCE MEDSYSTEMS, INC., Menlo Park, CA (US)

(72) Inventors: Mina M. Leung, Mountain View, CA (US); Jeff Tillack, Foster City, CA (US); Stephen H. Diaz, Palo Alto, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 95 days.

(21) Appl. No.: 16/824,625

(22) Filed: Mar. 19, 2020

(65) Prior Publication Data
US 2020/0297942 A1    Sep. 24, 2020

Related U.S. Application Data

(60) Provisional application No. 62/820,599, filed on Mar. 19, 2019.

(51) Int. Cl.
| | |
|---|---|
| *A61M 5/34* | (2006.01) |
| *A61M 5/32* | (2006.01) |
| *A61M 5/46* | (2006.01) |
| *A61M 5/31* | (2006.01) |

(52) U.S. Cl.
CPC .......... *A61M 5/344* (2013.01); *A61M 5/3202* (2013.01); *A61M 5/3293* (2013.01); *A61M 5/347* (2013.01); *A61M 5/46* (2013.01); *A61M 2005/312* (2013.01)

(58) Field of Classification Search
CPC .................. A61M 5/46; A61M 5/3202; A61M 2005/3267; A61M 5/3272
See application file for complete search history.

(56) References Cited

U.S. PATENT DOCUMENTS

| | | | | | |
|---|---|---|---|---|---|
| 5,176,650 | A | * | 1/1993 | Haining | A61M 25/0631 604/164.08 |
| 5,242,401 | A | * | 9/1993 | Colsky | A61M 5/347 604/110 |
| 5,250,026 | A | * | 10/1993 | Ehrlich | A61M 37/0069 604/117 |
| 5,267,973 | A | * | 12/1993 | Haber | A61M 5/322 604/110 |
| 5,318,536 | A | * | 6/1994 | Williams | A61M 5/322 604/110 |
| 5,318,547 | A | * | 6/1994 | Altschuler | A61M 5/315 604/263 |
| 5,429,612 | A | * | 7/1995 | Berthier | A61M 5/3257 604/110 |
| 5,591,138 | A | * | 1/1997 | Vaillancourt | A61M 5/3271 604/263 |
| 2009/0259180 | A1 | * | 10/2009 | Choi | A61M 5/46 604/117 |

(Continued)

*Primary Examiner* — William R Carpenter
(74) *Attorney, Agent, or Firm* — Vista IP Law Group LLP

(57) ABSTRACT

An injection system includes a body member having a body connection member at a distal end thereof. The system also includes a needle hub assembly coupled to the distal end of the injection system body. The needle hub assembly includes a needle hub coupled to the body connection member, a needle coupled to the needle hub, and a spacer removably coupled to the needle hub. The spacer reduces an exposed length of the needle.

7 Claims, 15 Drawing Sheets

(56) References Cited

U.S. PATENT DOCUMENTS

2011/0048174 A1\* 3/2011 Lin .................. A61M 37/0084
  606/186
2011/0319817 A1\* 12/2011 Rubinstein ............ A61M 5/326
  604/110

\* cited by examiner

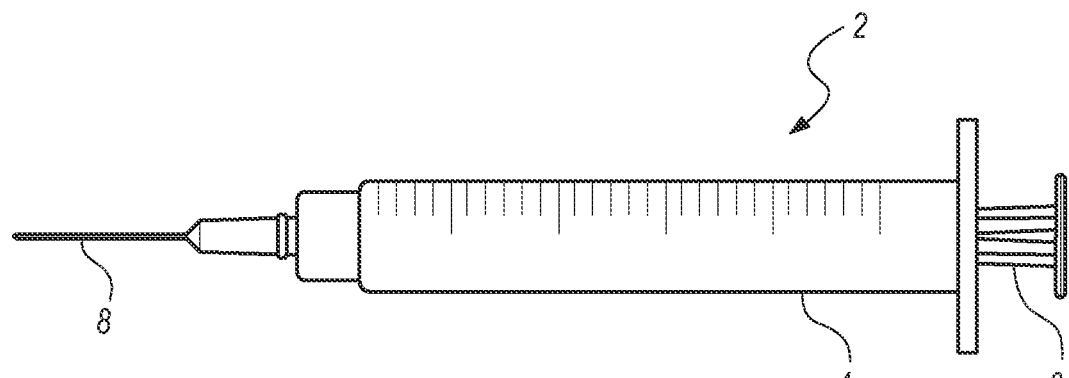
PRIOR ART   *FIG. 1A*
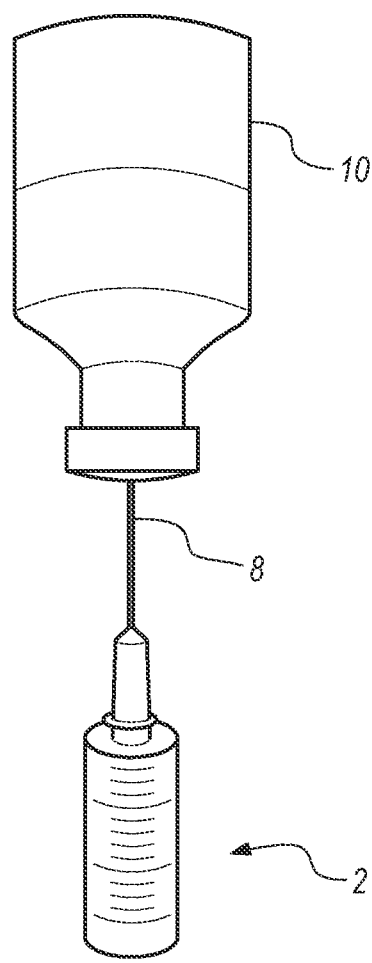
PRIOR ART   *FIG. 1B*

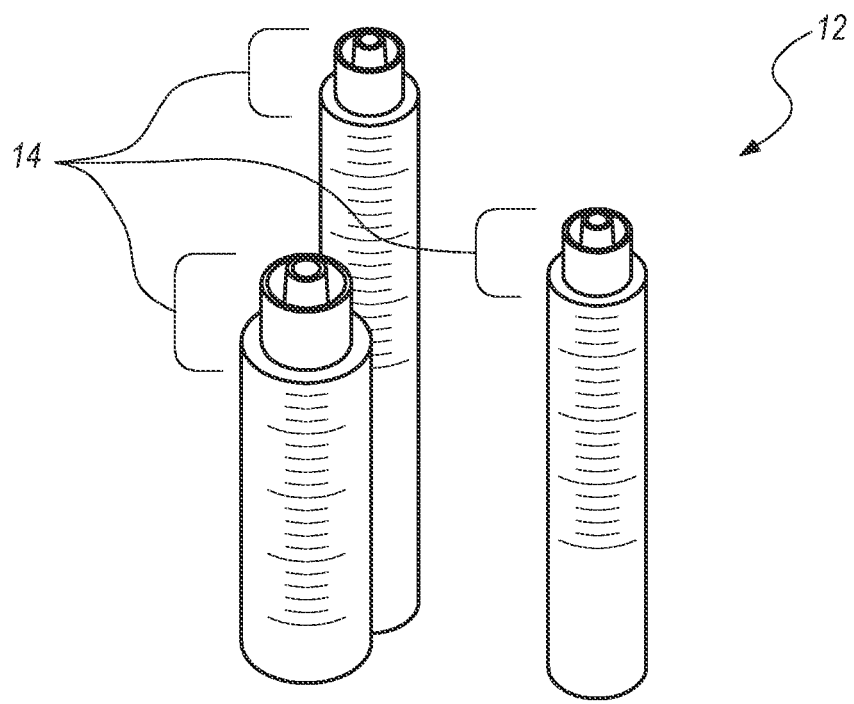
PRIOR ART  *FIG. 2A*
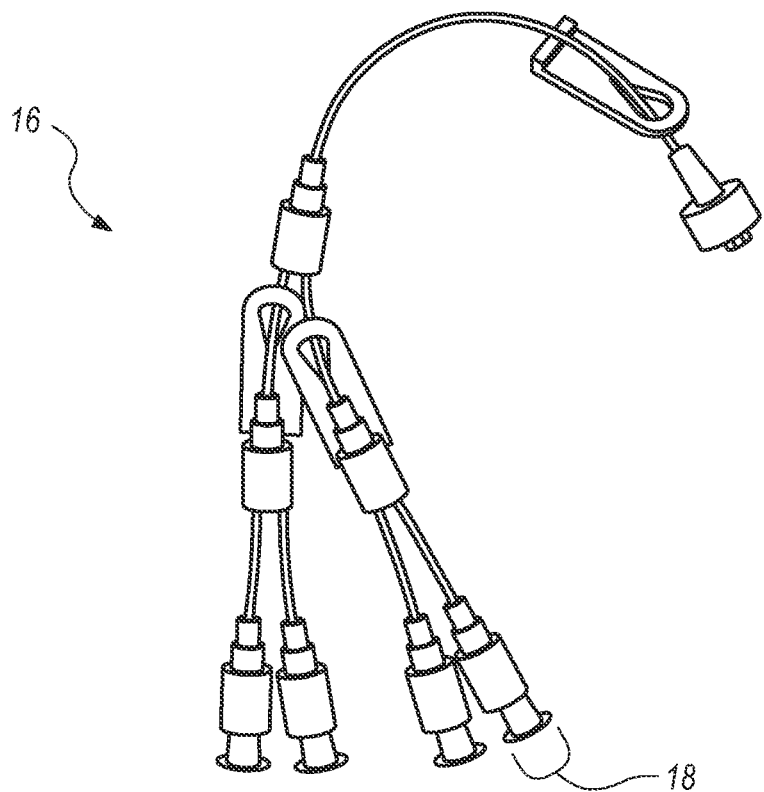
PRIOR ART  *FIG. 2B*

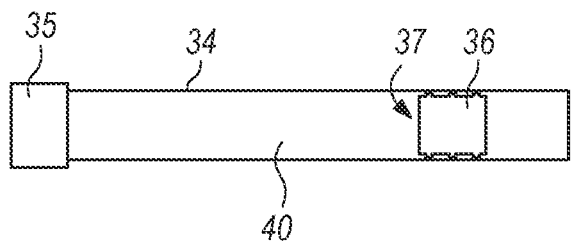
PRIOR ART  FIG. 5A
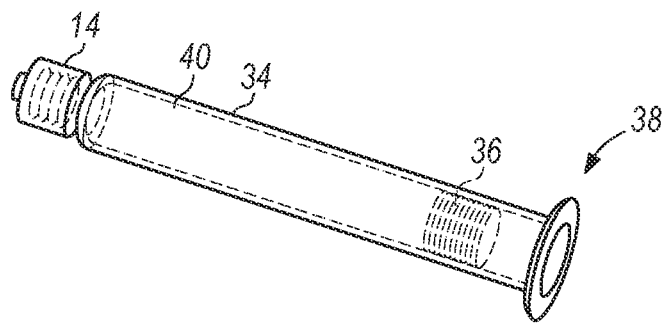
PRIOR ART  FIG. 5B
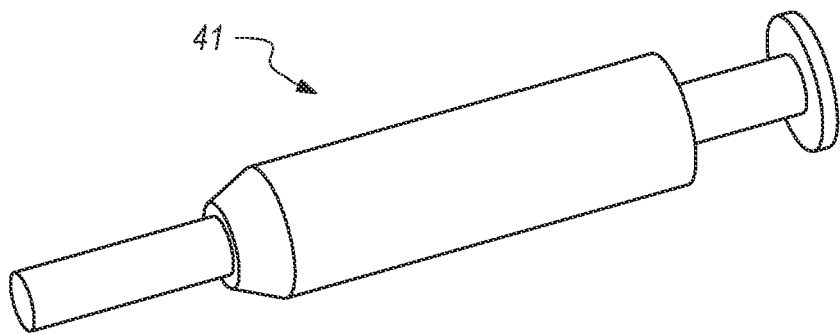
PRIOR ART  FIG. 5C

SYSTEM AND METHOD FOR ADJUSTABLE LENGTH NEEDLE

The present application claims priority to (1) U.S. Provisional Patent Application Ser. No. 62/820,599, filed on Mar. 19, 2019, and entitled "SYSTEM AND METHOD FOR ADJUSTABLE LENGTH NEEDLE." This application includes subject matter similar to the subject matter described in the following co-owned U.S. patent applications: (2) U.S. Utility patent application Ser. No. 14/696, 342, filed Apr. 24, 2015 and entitled "SYSTEM AND METHOD FOR SAFETY SYRINGE"; (3) U.S. Utility patent application Ser. No. 14/543,787, filed Nov. 17, 2014 and entitled "SYSTEM AND METHOD FOR DRUG DELIVERY WITH A SAFETY SYRINGE"; and (4) U.S. Utility patent application Ser. No. 14/321,706, filed Jul. 1, 2014 and entitled "SAFETY SYRINGE." The contents of the above-mentioned applications are fully incorporated herein by reference as though set forth in full.

FIELD OF THE INVENTION

The present invention relates generally to injection systems, devices, and processes for facilitating various levels of control over injection target access, and more particularly to injection systems and methods related to injection in healthcare environments. Even more particularly, the present invention relates to injection systems, devices, and processes for adjusting a length of a needle in an injection system.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling.

The use of needle injection configurations, on the other hand, carries with it the risk of a sharp needle contacting or poking a person or structure that is not desired. For this reason, so called "safety syringes" have been developed. One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety. Other "safety syringes" are described in U.S. patent application Ser. Nos. 14/696,342, 14/543,787, 14/321,706, 62/416,102, 62/431,382, and 62/480,276, the contents of which have been incorporated herein by reference.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface (14). Liquid medicine may reside in the volume, or medicine reservoir, (40) between the distal seal (35) and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as the system (41) featured in FIG. 5C, which attempts to meet all of the standards, or at least a portion thereof, with one solution by including most or all parts needed to perform an injection (body, stopper, needle, plunger, etc.) As a result of trying to meet these standards for many different scenarios, such products may have significant limitations (including some of those described above in reference to FIGS. 3-4B) and relatively high inventory and utilization expenses.

Regardless of the type of injection system, the ability to adjust/select the length of a needle in a preassembled injection system can provide many advantages. Various medications are ideally injected into different patient tissue targets and tissue depths. For instance, the influenza vaccine is typically administered intramuscularly, i.e., deeper (e.g., about 1 inch) into the muscular tissue (e.g., deltoid muscle) of a patient. On the other hand, insulin is typically administered subcutaneously, i.e., less deep (e.g., about 0.5 inch) between the dermis/epidermis and muscular tissue (e.g., the abdomen) of a patient. While the influenza vaccine and insulin are typically administered in these targets and target depths, these medicines may be administered in different targets and target depths on the patient's body depending on the clinical situation, patient, and/or user. Existing injection systems require selection and attachment of different needles to injection system bodies in order to vary the length of the needle in an injection system to conform to the medication to be delivered. Selection and attachment of needles to injection system bodies introduces opportunities for user error and increases the time for injections, the risk of unintentional needle sticks, and corresponding patient anxiety. Alternatively, preassembled injection systems can be divided into species with different needle lengths. Having different species of preassembled injection systems also introduces opportunities for user error and complexity to medical equipment supply chains. The ability to adjust/select the length of the needle and a preassembled injection system reduces user error and patient anxiety, and streamlines medical equipment supply chains.

There is a need for injection systems that address the shortcomings of currently-available configurations. In particular, there is a need for preassembled injection systems with adjustable length needles. Further, there is a need for preassembled injection systems in which a needle length can be adjusted/selected either during or after removal of rigid needle shield while minimizing opportunities for user error.

SUMMARY

Embodiments are directed to injection systems. In particular, the embodiments are directed to preassembled injection systems with adjustable/selectable needle lengths.

In one embodiment, an injection system includes a body member having a body connection member at a distal end thereof. The system also includes a needle hub assembly coupled to the distal end of the injection system body. The needle hub assembly includes a needle hub coupled to the body connection member, a needle coupled to the needle hub, and a spacer removably coupled to the needle hub. The spacer reduces an exposed length of the needle.

In one or more embodiments, removing the spacer from the needle hub increases the exposed length of the needle. The body connection member may include an annular recess, and the needle hub may include a ring configured to retain the needle hub on the body connection member. The body connection member may include an annular ledge adjacent the annular recess, and the ring may be configured to move past the annular ledge in a proximal direction. The needle hub may include a space configured to house the ring to prevent movement of the ring along a longitudinal axis relative to the needle hub.

In one or more embodiments, the needle hub includes a detent, and the spacer includes a slot configured to interact with the detent to temporarily prevent movement of the spacer along a longitudinal axis relative to the needle hub, thereby removably coupling the spacer to the needle hub. The detent and the slot may be configured such rotating the spacer relative to the needle hub uncouples the space from the needle hub.

In one or more embodiments, the system also includes a rigid needle shield removably coupled to the spacer. The needle hub, the spacer, and the rigid needle shield may be configured such that pulling the rigid needle shield relative to the body member releases the rigid needle shield from the spacer and rotating the spacer relative to the body member releases the spacer from the needle hub. The spacer may include an annular recess, and the rigid needle shield may include an annular protrusion configured to interfere with the annular recess to temporarily prevent removal of the rigid needle shield along a longitudinal axis relative from the spacer.

In one or more embodiments, an inner surface of the spacer forms a seal against an outer surface of the needle hub. The system may also include a gasket disposed between the distal end of the body member and an inner surface of the needle hub. The gasket may be configured to prevent contamination of an interior of the body member.

In another embodiment, an injection system includes a body member having a body connection member at a distal end thereof. The system also includes a needle hub assembly coupled to the distal end of the injection system body. The needle hub assembly includes a needle hub coupled to the body connection member, a needle coupled to the needle hub, and a spacer movably coupled to the needle hub. Moving the spacer along a longitudinal axis modifies an exposed length of the needle.

In one or more embodiments, the system also includes an actuator configured to move the spacer along the longitudinal axis. The actuator may include a plurality of ratchet teeth on the needle hub defining a plurality of spaces, and a pawl coupled to the spacer. The pawl may be configured to movably lodge in each of the plurality of spaces. Moving the pawl along the longitudinal axis may move the spacer along the longitudinal axis.

In one or more embodiments, the system also includes a gasket disposed between the distal end of the body member and an inner surface of the needle hub. The gasket may be configured to prevent contamination of an interior of the body member. The system may also include an O-ring disposed between a distal end of the needle hub and an inner surface of the spacer. The O-ring may be configured to prevent contamination of an interior of the spacer.

In still another embodiment, an injection system includes a body member having a body connection member at a distal end thereof. The system also includes a needle hub assembly coupled to the distal end of the injection system body. The needle hub assembly includes a needle hub coupled to the body connection member, a needle coupled to the needle hub, and a spacer movably coupled to the needle hub. Rotating the spacer about a longitudinal axis modifies an exposed length of the needle.

In one or more embodiments, the needle hub includes a grooved portion, and the spacer includes a radially inwardly extending member configured to interfere with the grooved portion of the needle hub to control movement of the space along the longitudinal axis. The grooved portion may define a helical groove. The grooved portion may include a first flattened end, and the radially inwardly extending member may be aligned with the helical groove and not aligned with the first flattened end.

In one or more embodiments, the first flattened end includes a radially outwardly extending detent configured to retain the radially inwardly extending member in the first flattened end. The radially inwardly extending member may include a radially inwardly extending bump configured to interfere with the radially outwardly extending detent to retain the radially inwardly extending member in the first flattened end. The grooved portion may include a second flattened end opposite of the first flattened end. The radially inwardly extending member may not be aligned with the second flattened end. The second flattened end may include a radially outwardly extending detent configured to retain the radially inwardly extending member in the second flattened end.

In one or more embodiments, the grooved portion defines two helical grooves, and the spacer includes two radially inwardly extending members, including the radially inwardly extending member. The system may include an O-ring disposed between an inner surface of the spacer and an outer surface of the needle hub to form a seal therebetween. The system may include a gasket disposed between an outer surface of the needle and an inner surface of the needle hub to form a seal therebetween.

The aforementioned and other embodiments of the invention are described in the Detailed Description which follows.

BRIEF DESCRIPTION OF THE DRAWINGS

The drawings described below are for illustration purposes only. The drawings are not intended to limit the scope of the present disclosure.

The foregoing and other aspects of embodiments are described in further detail with reference to the accompanying drawings, in which the same elements in different figures are referred to by common reference numerals, wherein:

FIGS. 1A to 5C illustrate various aspects of conventional injection syringe configurations.

FIGS. 6 to 8C and 10 illustrate various aspects of an adjustable/selectable injection system according to some embodiments.

Figure 3:
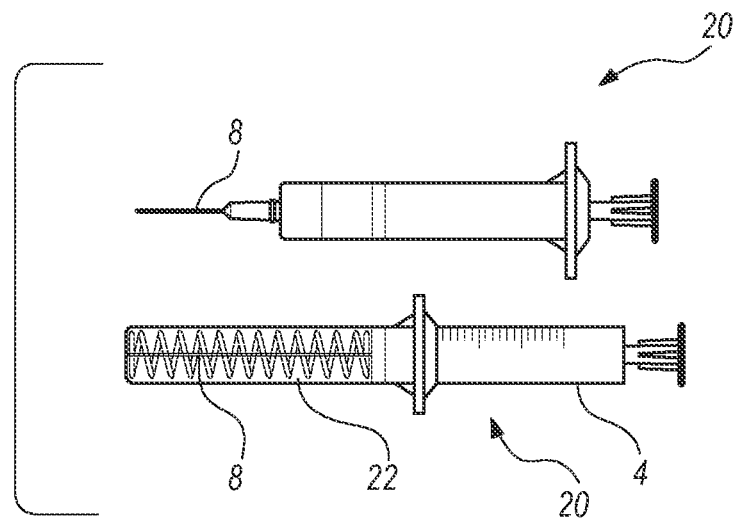
Figure 4A:
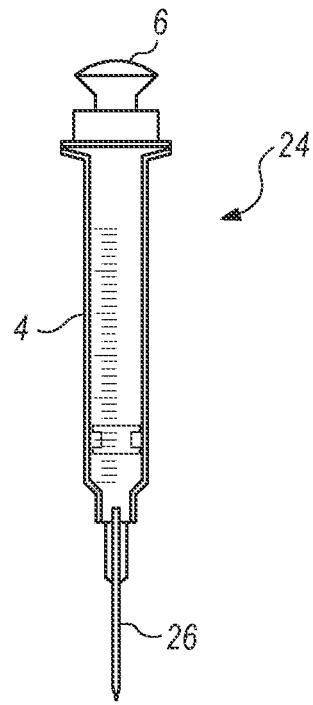
Figure 4B:
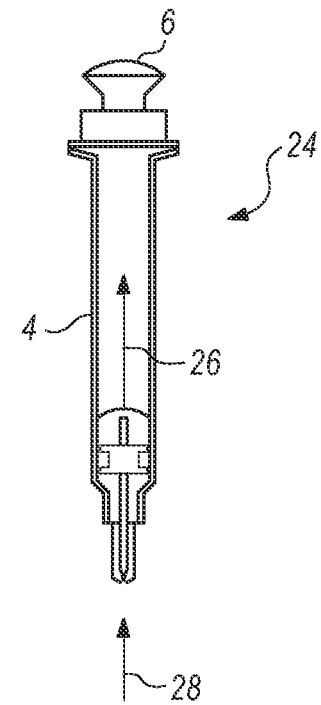

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Removable Needle Length Spacer

Figure 6:
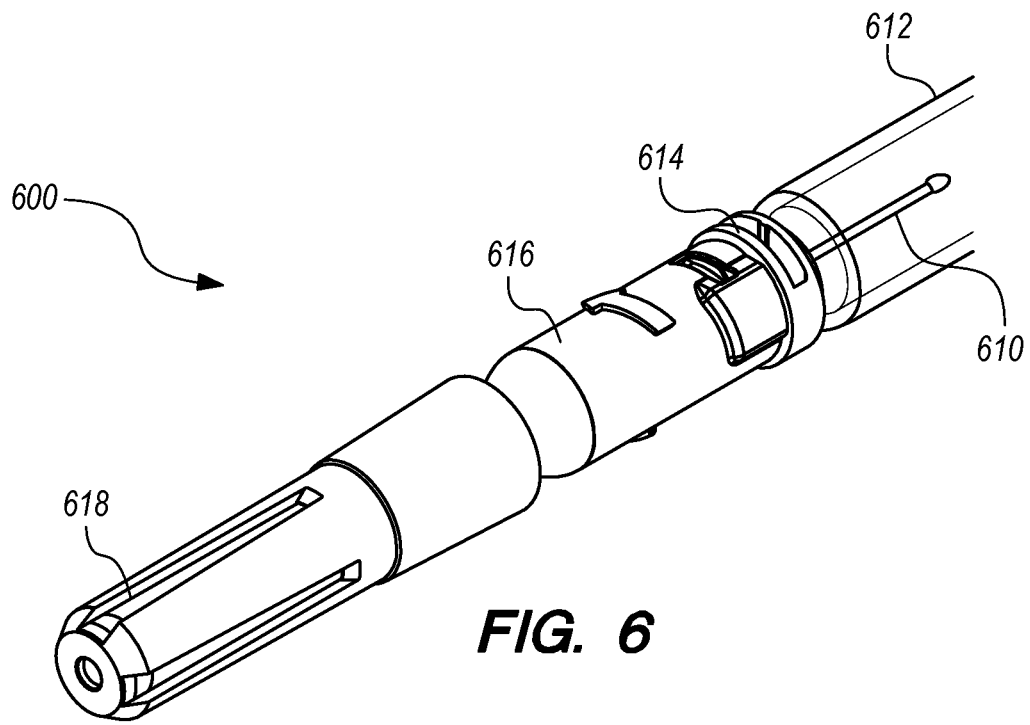

FIG. 6 depicts the distal end of a preassembled injection system 600 including a single needle 610 with multiple exposed length configurations according to some embodiments. The injection system 600 includes an injection system body 612, which may be, for example, a syringe body or a cartridge. The injection system 600 may be a traditional injection system or a safe injection system that retracts the needle at least partially inside the needle hub 614 and/or injection system body 612 after injection to reduce the risk of unintentional needle sticks. Examples of safe injection systems are described in U.S. Utility patent application Ser. No. 14/696,342, which has been previously incorporated by reference herein.

The proximal end of the preassembled injection system 600, which may include components such as stopper members and a plunger rod, is not depicted or described in this specification because the components of the adjustable/selectable exposed needle length injection systems described herein are located at the distal end of the injection systems. The components of the adjustable/selectable exposed needle length injection systems described herein are usable/compatible with off the shelf injection system components such as injection system bodies, stopper members, and plunger rods. The components of the adjustable/selectable exposed needle length injection systems described herein are also usable/compatible with components configured to be compatible with off the shelf injection system components, such as those described in U.S. Utility patent application Ser. No. 14/696,342, which has been previously incorporated by reference herein.

Still referring to FIG. 6, the injection system 600 also includes a needle length spacer 616 which is passed over the distal end of the needle 610 and removably coupled to the needle hub 614. The needle 610 is coupled (removably in some embodiments) to the needle hub 614 through which the needle 610 extends. The injection system 600 also includes a rigid needle shield 618 removably coupled to the needle length spacer 616. Further details regarding the coupling of various components to each other are described below.

Figure 7:
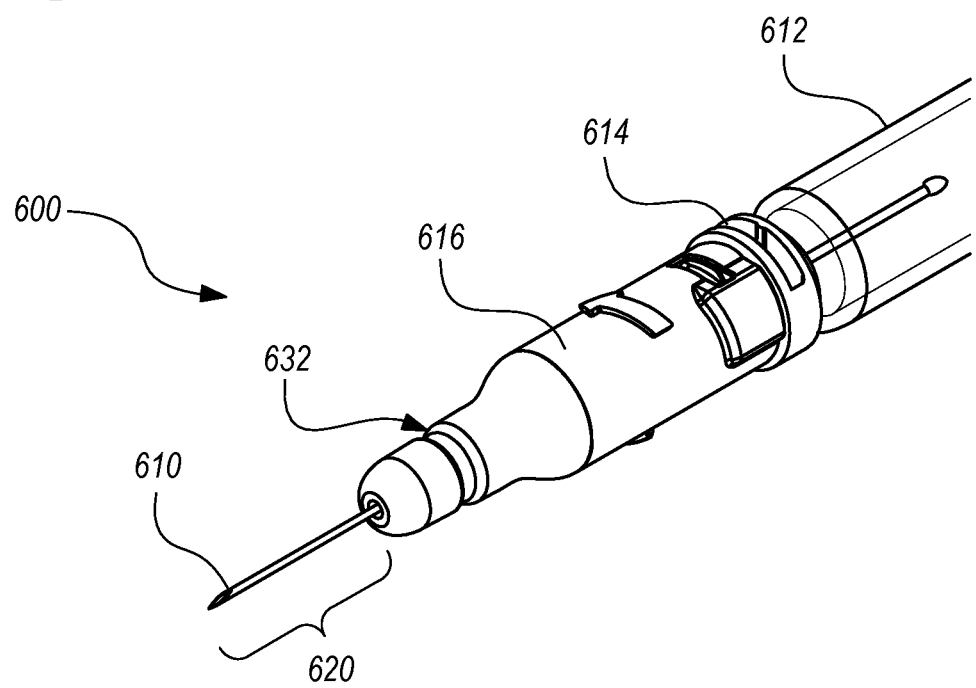

FIG. 7 depicts the preassembled injection system 600 with the rigid needle shield 618 removed. This places the injection system 600 in a short needle/subcutaneous configuration. The exposed length 620 of the needle 610 in the short configuration, which extends distally beyond the distal end of the needle length spacer 616, may be configured to be suitable for subcutaneous injection (e.g., approximately 0.5 inches). Removing the rigid needle shield 618 also exposes the sharp distal end of the needle 610.

Figure 8:
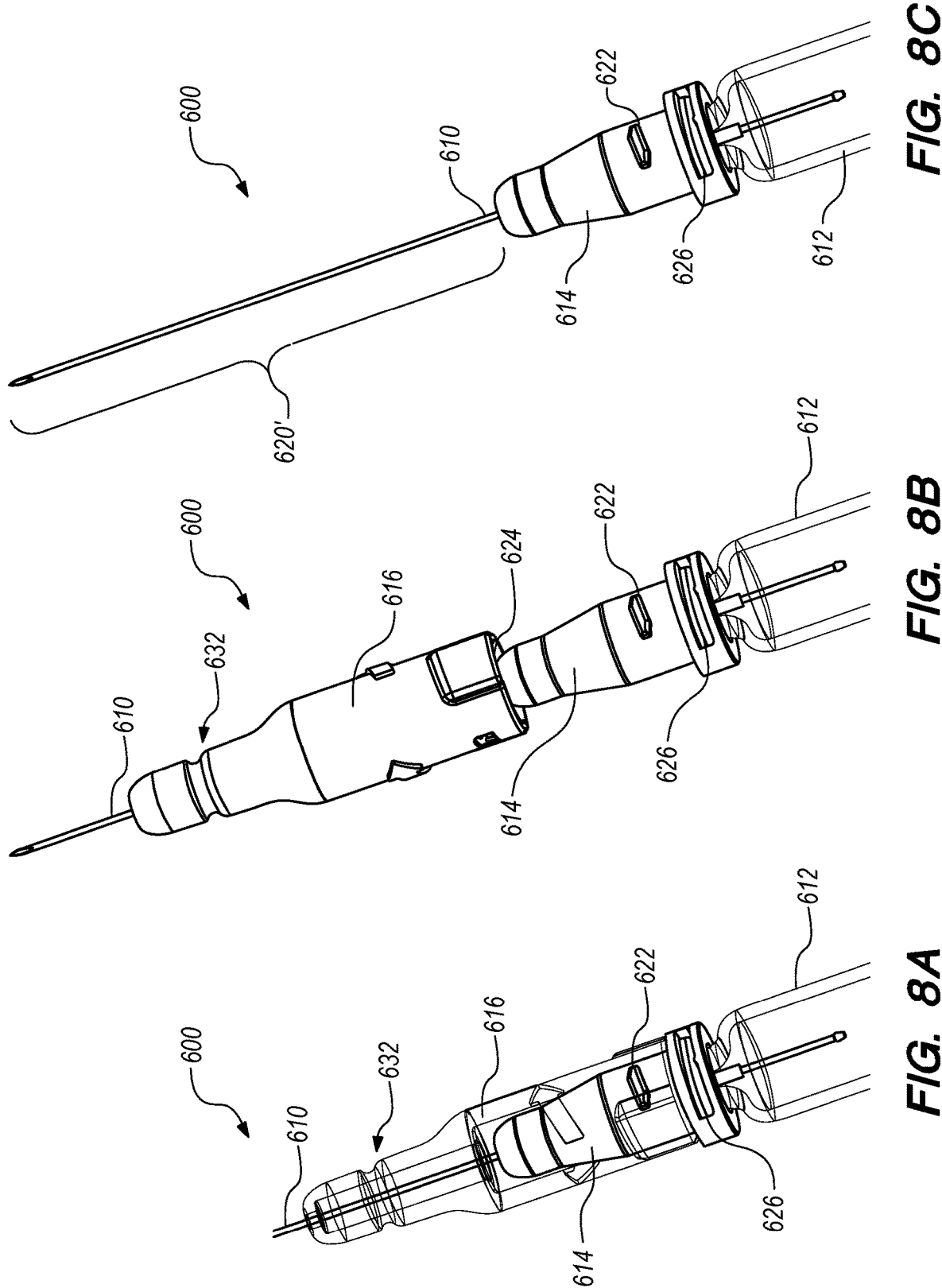

FIGS. 8A to 8C depict removal of the needle length spacer 616 from the injection system 600 after removal of the rigid needle shield 618 to convert the injection system 600 from a short needle/subcutaneous configuration to a long needle/intramuscular configuration. FIG. 8A depicts the injection system 600 in a short needle/subcutaneous configuration similar to the one depicted in FIG. 7. FIG. 8A depicts the needle length spacer 616 in shadow to depict the detent 622 on the needle hub 614 configured to temporarily prevent movement of the needle length spacer 616 along the longitudinal axis of the injection system 600 when the injection system 600 is in the short needle/subcutaneous configuration.

FIG. 8B depicts the needle length spacer 616 being removed from the needle hub 614. The needle length spacer 616 includes a longitudinal slot 624 hidden behind the rectangular protrusion on the removable spacer 616 that allows the needle length spacer 616 to be slid free from the detent 622 on the needle hub 614 when the slot 624 is rotationally aligned with the detent 622.

Accordingly, to convert the injection system 600 from a short needle/subcutaneous configuration (FIG. 8A) have to a long needle/intramuscular configuration (FIG. 8C), the needle length spacer 616 is rotated to align the slot 624 with the detent 622 and then pulled distally along the longitudinal axis of the injection system 600 to remove the needle length spacer 616 from the needle hub 614 and the injection system 600.

FIG. 8C depicts the injection system 600 in a long needle/intramuscular configuration. The injection system 600 is placed in the long needle configuration after complete removal of the needle length spacer 616 from the needle hub 614 and the needle 610. The exposed length 620' of the needle 610 in the long configuration, which extends distally beyond the distal end of the needle hub 614, may be configured to be suitable for intramuscular injection (e.g., approximately 1 inch).

Figure 9:
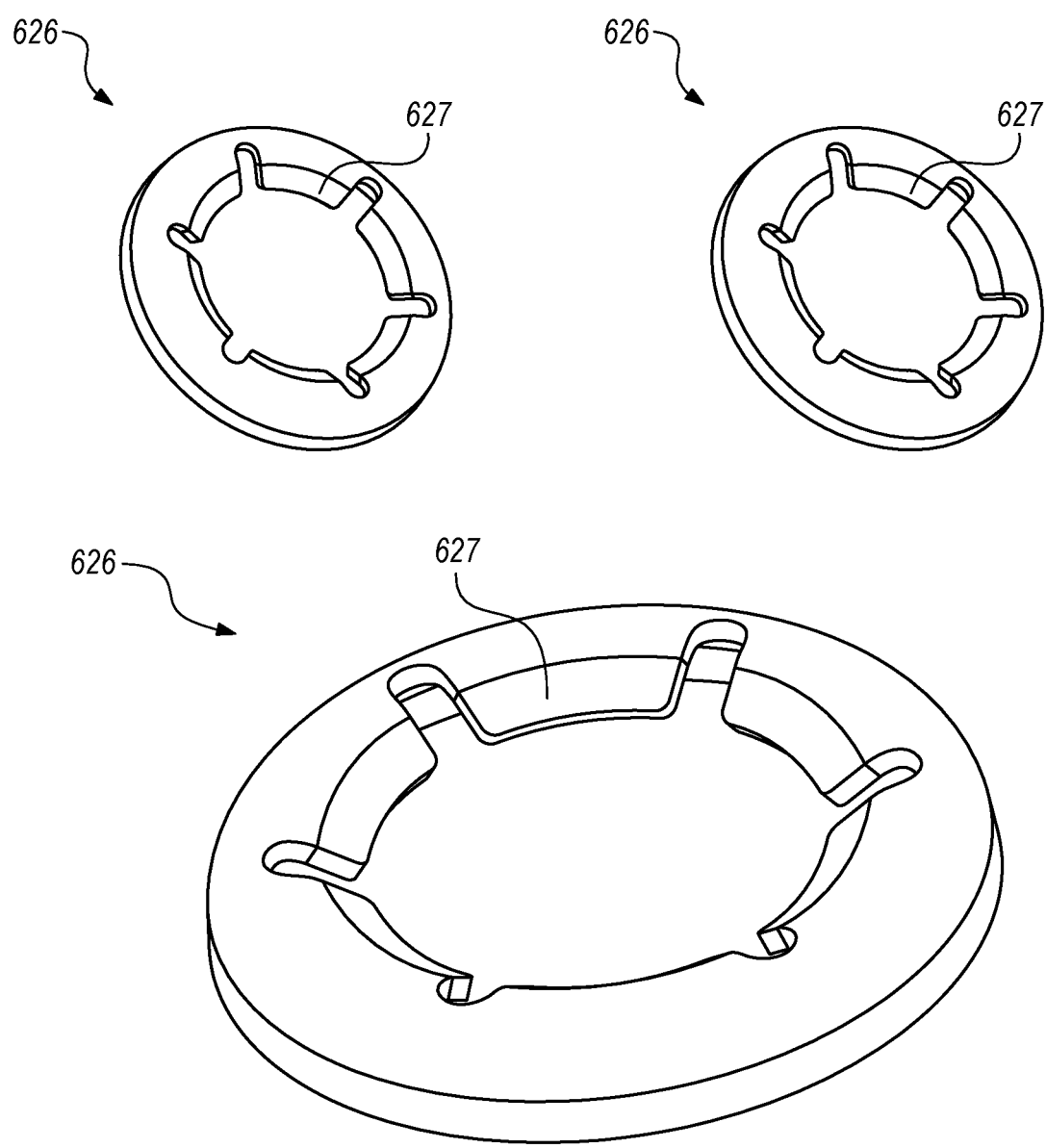
FIG. 9 depicts a retaining ring for use with adjustable/selectable injection systems according to some embodiments.
Figure 10:
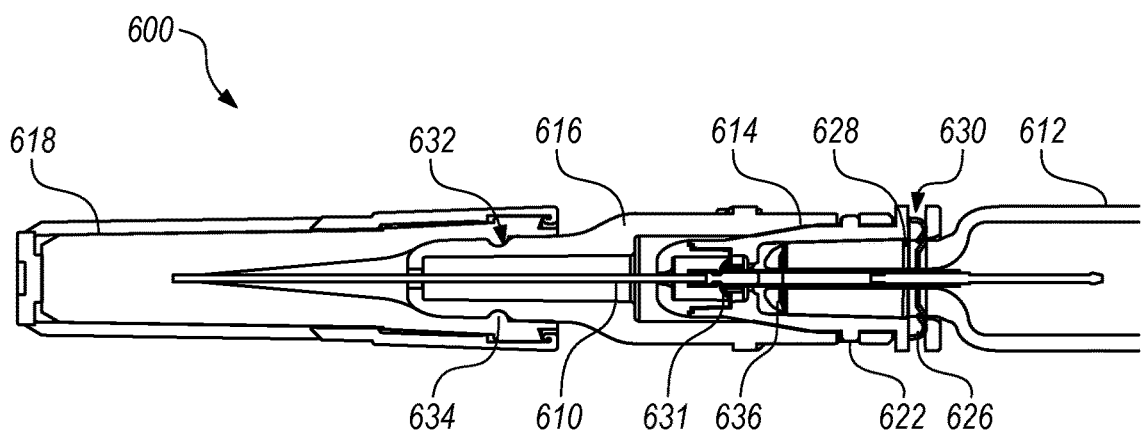

FIG. 9 depicts a metal retaining ring 626 for the use with a needle hub 614 of the preassembled injection system 600 depicted and described herein according to some embodiments. Because the metal retaining ring 626 includes teeth 627 that are biased in such a way to bend more readily in one direction compared to the opposite direction, the retaining ring 626 can slip proximally over an annular ledge 628 more easily at the distal end of the system body 612, while providing relatively more substantial resistance to removing the retaining ring 626 distally over the annular ledge 628, as shown in FIG. 10. There is a self-braking action that occurs between the teeth 627 and the system body 612 that helps resist the removal of the retaining ring 626 over the annular ledge 628. The teeth 627 tend to bind harder to the annular ledge 628 as more removal force is applied. This is due to the non-shallow angle that is formed between the teeth 627 and the annular ledge 628 after assembly, which increases friction between the teeth 627 and the annular ledge 628 with increasing removal force, thereby preventing the teeth 627 from skipping over the annular ledge 628. The domed curvature of the teeth 627 and the surrounding metal of the retaining ring 626 lends structural strength to the teeth 627, which thereby squeeze the annular ledge 628 with substantial radial force, and helps to reinforce the self-braking action and help the teeth 627 to resist skipping over the annular ledge 628. Because the needle hub 614 defines a space 630 in which the retaining ring 626 is disposed and because the system body 612 defines an annular recess configured to receive the retaining ring 626, interference between the annular ledge 628 and the retaining ring 626 allows the needle hub 614 to be mounted onto the system body 612 in the proximal direction while preventing removal of the needle hub 614 from the system body 612. The metal retaining ring 626 has greater hardness and elasticity compared to the system body 612 due to its metallic composition.

FIG. 10 depicts a preassembled injection system 600 according to some embodiments. The injection system 600 includes a needle 610, a system body 612, a needle hub 614, a needle length spacer 616, and a rigid needle shield 618. The needle hub 614 is coupled to the system body 612 via a radial interference fit between the retaining ring 626 in the needle hub 614 and an annular ledge 628 on the system body 612. The needle length spacer 616 is removably coupled to the needle hub 614 via an interference fit between the detent 622 on the needle hub 614 and the portion of the needle length spacer 616 defining the slot 624 (see FIG. 8B). The needle 610 is removably coupled to the needle hub 614 via a pair of needle latches 631 as described in U.S. Utility patent application Ser. No. 14/696,342, which has been previously incorporated by reference herein.

The needle 610, the needle hub 614, and the needle length spacer 616 formed a needle hub assembly. The rigid needle shield 618 is removably coupled to the needle length spacer 616 via an interference fit between an annular recess 632 on the needle length spacer 616 and an annular protrusion 634 on an inner surface of the rigid needle shield 618. The rigid needle shield 618 can be removed from the needle length spacer 616 by pulling the rigid needle shield 618 and the needle length spacer 616 apart from each other along the longitudinal axis of the injection system 610 with sufficient force to overcome the interference fit between the annular recess 632 and the annular protrusion 634. As described above, the detent 622 on the needle hub 614 prevents the needle length spacer 616 from pulling apart from the needle hub 614 until the needle length spacer 660 is rotated relative to the needle hub 614 two aligned the detent 622 with the slot 624 on the needle length spacer 616. Accordingly, the rigid needle shield 618 can be removed from the rest of the injection system 600 by pulling the rigid needle shield 618 in a distal direction. Further, the needle length spacer 616 can be removed from the rest of the injection system 600 (with or without the rigid needle shield 618) by rotating the needle length spacer 616 to align the detent 622 with the slot 624 and pulling the needle length spacer 616 in a distal direction. While FIGS. 8A to 8C show removal of the needle length spacer 616 from the rest of the injection system 600 after the rigid needle shield 618 has been removed, the needle length spacer 616 can be removed from the rest of the injection system 600 along with the rigid needle shield 618, which would remain attached to the needle length spacer 616. This allows a user to selectively remove various components of the injection system 600 to place the system 600 in either the short needle (remove only the rigid needle shield 618 by pulling) or the long needle (remove the needle length spacer 616 along with the rigid needle shield 618 by twisting and pulling) while minimizing the occurrence of an unintentional needle sticks. On the other hand, if a user places the injection system 600 in either the short needle or the long needle configuration by mistake, the user can place the injection system 600 in the other configuration by either removing and/or replacing the needle length spacer 616.

The injection system 600 also includes a gasket 636 disposed between the distal end of the system body 612 and an inner surface of the needle hub 614. The gasket is configured to prevent contamination of the interior of the system body 612 and the injectable contained therein.

By allowing a user to select between short and long needle configurations, the preassembled injection system 600 described above facilitates use of a single preassembled injection system for both subcutaneous (short needle configuration) and intramuscular (long needle configuration) injections. The preassembled injection system 600 allows removal of either the rigid needle shield 618 (short needle configuration) or the needle length adapter 616 along with the rigid needle shield 618 (long needle configuration) from the shipping configuration with the rigid needle shield 618 attached. Selection of a short or long needle configuration from the shipping configuration minimizes the risk of inadvertent needle sticks compared to systems that involve manipulation of components near the tip of the needle 610. Further, the preassembled injection system 600 allows a user to transition between short and long needle configurations after removal of the rigid needle shield 618 in case the wrong configuration is selected when removing the rigid needle shield 618.

While the preassembled injection system 600 described above may be selectable between a 0.5 inches short configuration and a 1 inch long configuration, other embodiments include components of different sizes that can result in two configurations with different lengths. While the preassembled injection system 600 described above includes a luer taper connector, other types of connectors may be used to couple the needle hub to the injection system body. While the preassembled injection system 600 described above includes the needle latches 631 of a safe injection system, other embodiments may include a standard needle hub assemblies without needle retraction features.

Movable Needle Length Spacer

Figure 11:
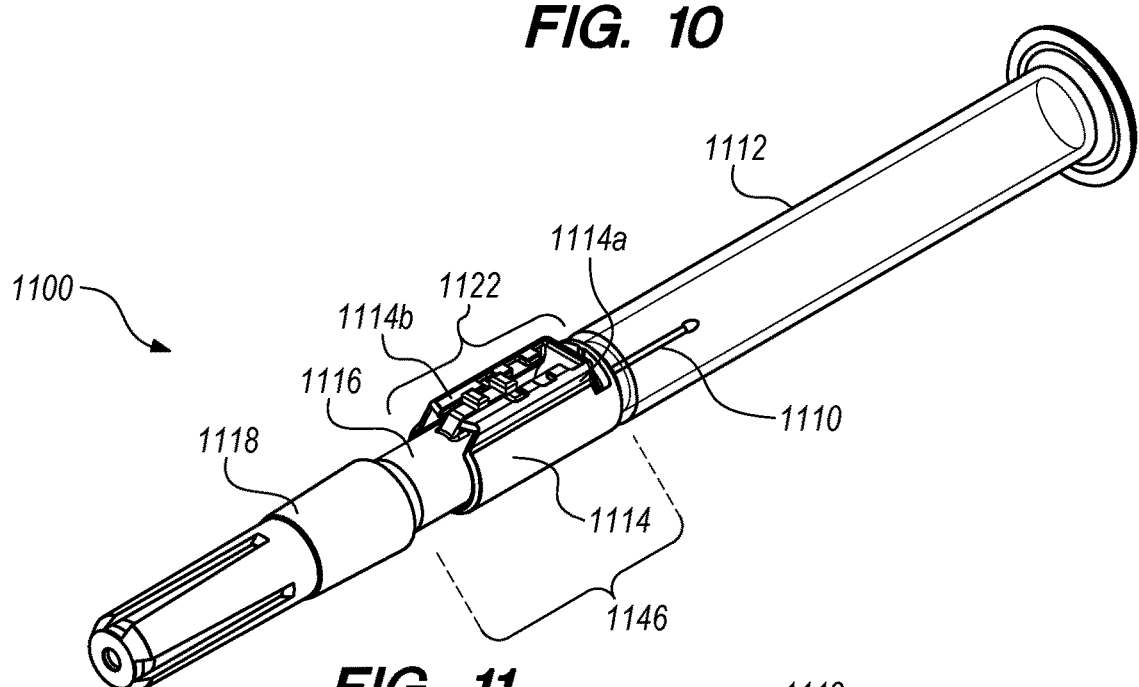
FIGS. 11 to 15 illustrate various aspects of an adjustable/selectable injection system according to some embodiments.

FIG. 11 depicts a preassembled injection system 1100 including a single needle 1110 with multiple exposed length configurations according to some embodiments. The injection system 1100 includes an injection system body 1112, which may be, for example, a syringe body or a cartridge. The injection system 1100 may be a traditional injection system or a safe injection system that retracts the needle at least partially inside the needle hub 1114 and/or injection system body 1112 after injection to reduce the risk of unintentional needle sticks. Examples of safe injection systems are described in U.S. Utility patent application Ser. No. 14/696,342, which has been previously incorporated by reference herein.

Other components of the injection system 1100, such as stopper members and a plunger rod, are not depicted or described in this specification because the components of the adjustable/selectable exposed needle length injection systems described herein are located at the distal end of the injection systems. The components of the adjustable/selectable exposed needle length injection systems described herein are usable/compatible with off the shelf injection system components such as injection system bodies, stopper members, and plunger rods. The components of the adjustable/selectable exposed needle length injection systems described herein are also usable/compatible with components configured to be compatible with off the shelf injection system components, such as those described in U.S. Utility patent application Ser. No. 14/696,342, which has been previously incorporated by reference herein.

Still referring to FIG. 11, the injection system 1100 also includes a needle hub assembly 1146 having a movable needle length spacer 1116 which is movably coupled to the needle hub 1114. The needle 1110 is coupled (removably in some embodiments) to the needle hub 1114 through which the needle 1110 extends. The needle hub 1114 comprises a raised structure 1114a having a flattened surface 1114b. The injection system 1100 also includes a rigid needle shield 1118 removably coupled to the needle length spacer 1116. Moreover, the injection system 1100 includes an actuator 1122 configured to move the needle length spacer 1116 along the longitudinal axis of the injection system 1100 thereby modifying/adjusting an exposed length 1120 of the needle 1110 (see FIGS. 12 to 14B). Further details regarding the coupling of various components to each other are described below.

Figure 12:
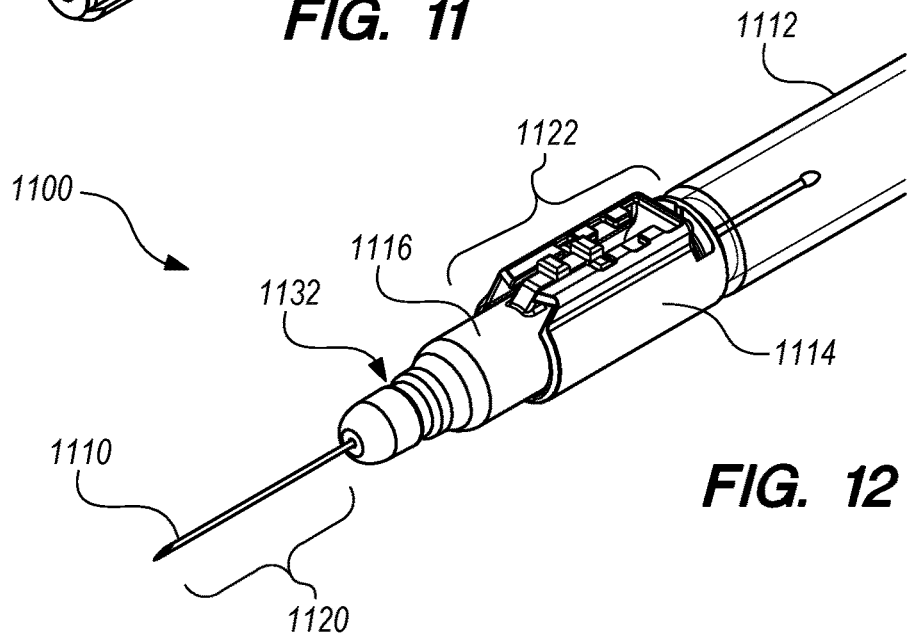

FIG. 12 depicts the injection system 1100 with the rigid needle shield 1118 removed (see FIG. 11). Removing the rigid needle shield 1118 exposes the sharp distal end of the needle 1110. The injection system depicted in FIG. 12 is in a short needle/subcutaneous configuration. The exposed length 1120 of the needle 1110 in the short configuration, which extends distally beyond the distal end of the needle length spacer 1116, may be configured to be suitable for subcutaneous injection (e.g., approximately 0.5 inches).

Figure 13A:
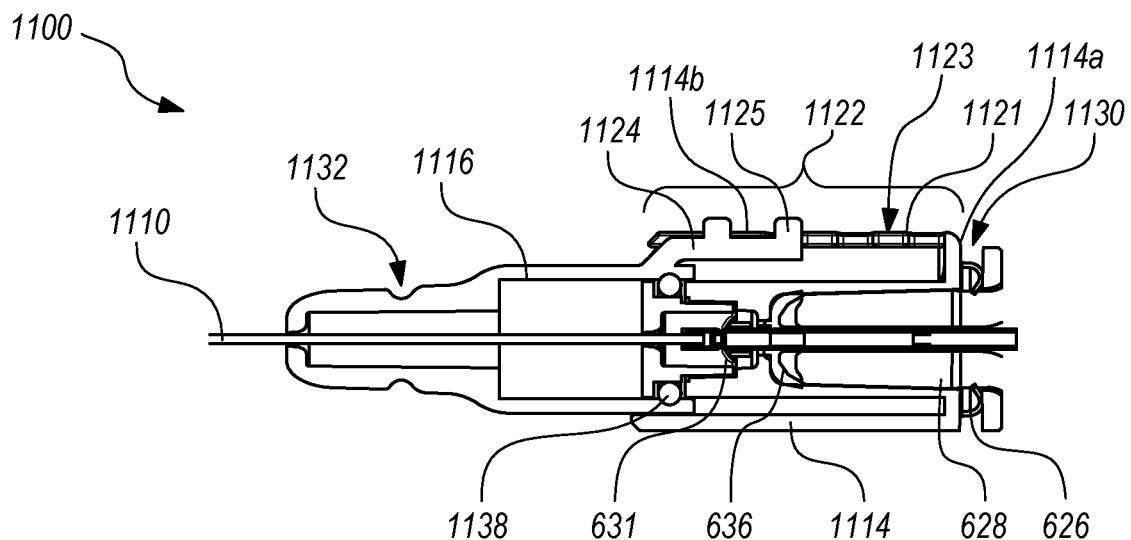
Figure 13B:
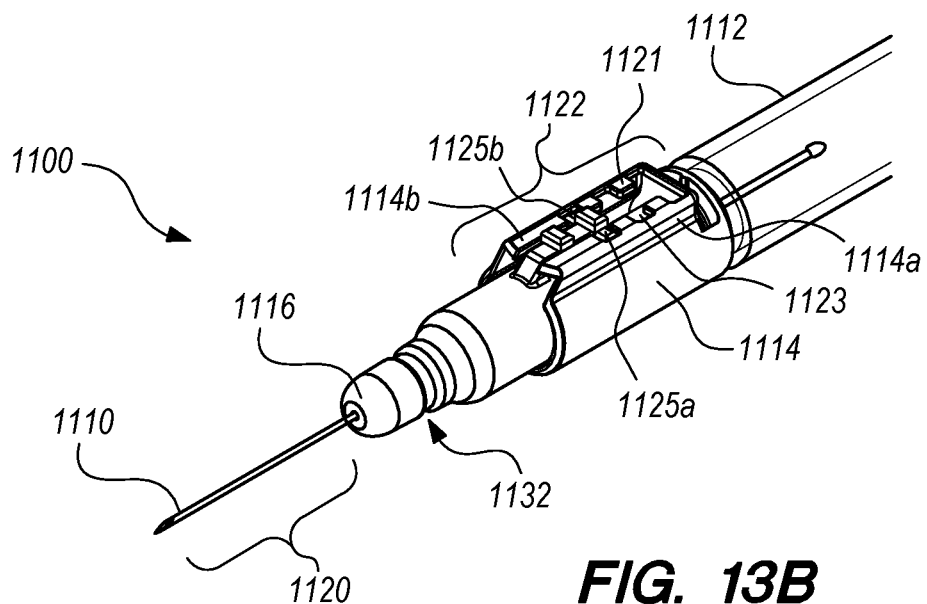

FIGS. 13A and 13B depict the injection system 1100 in a short needle/subcutaneous configuration. FIG. 13A depicts the actuator 1122 in detail. The actuator 1122 includes a plurality of ratchet teeth 1121 disposed on the flattened surface 1114b of the raised structure 1114a of the needle hub 1114 that define a plurality of spaces 1123. The actuator 1122 also includes a pawl 1124 coupled to the needle length spacer 1116. The pawl 1124 includes two extensions 1125 on its proximal end that are spaced to fit inside adjacent spaces 1123 on the needle hub 1114. In FIGS. 13A and 13B, the pawl 1124 is disposed in its distal most position relative to the needle hub 1114, thereby placing the actuator 1122 and the needle length spacer 1116 in their respective distal most positions. This in turn places the injection system 1100 in its short needle/subcutaneous configuration in which the exposed length 1120 of the needle 1110 is reduced by the overlapping needle length spacer 1116. Interference between the extensions 1125 and the ratchet teeth 1121 prevent relative movement of the needle length spacer 1116 and the needle hub 1114 along the longitudinal axis of the injection system 1100. Additionally, as shown in FIG. 13B, the plurality of ratchet teeth 1121 include a plurality of pairs of opposing ratchet teeth disposed on the flattened surface 1114b of the raised structure 1114a of the needle hub 1114, defining a plurality of pairs of opposing discrete spaces 1123. The pawl 1124 includes a pair of opposing laterally extending pegs 1125a and 1125b configured to interfere with each of the plurality of pairs of opposing discrete spaces 1123 to removably position the spacer 1116 relatively to the needle hub 1114.

FIGS. 13A and 13B also depict a retaining ring 626, similar to the one described above for use in the preassembled injection system 600, for the use with the needle hub 1114 of the preassembled injection system 1100. Because the retaining ring 626 includes teeth 267 that bend more readily in one direction compared to the opposite direction, the retaining ring 626 can slip proximally over an annular ledge 628 at the distal end of the system body 1112, while providing substantial resistance to removing the retaining ring 626 distally over the annular ledge 628. Because the needle hub 1114 defines a space 1130 in which the retaining ring 626 is disposed and because the system body 1112 defines an annular recess configured to receive the retaining ring 626, interference between the annular ledge 628 and the retaining ring 626 allows the needle hub 1114 to be mounted onto the system body 1112 in the proximal direction while preventing removal of the needle hub 1114 from the system body 1112.

The injection system 1100 also includes a gasket 636 disposed between the distal end of the system body 1112 and an inner surface of the needle hub 1114. The gasket is configured to prevent contamination of the interior of the system body 1112 and the injectable contained therein. The injection system 1100 further includes an O-ring 1138 disposed between a distal end of the needle hub 1114 and an inner surface of the needle length spacer 1116. The O-ring 1138, in conjunction with the rigid needle shield 1118, are configured to prevent contamination of respective interiors of the needle length spacer 1116 and the needle hub 1114.

Figure 14A:
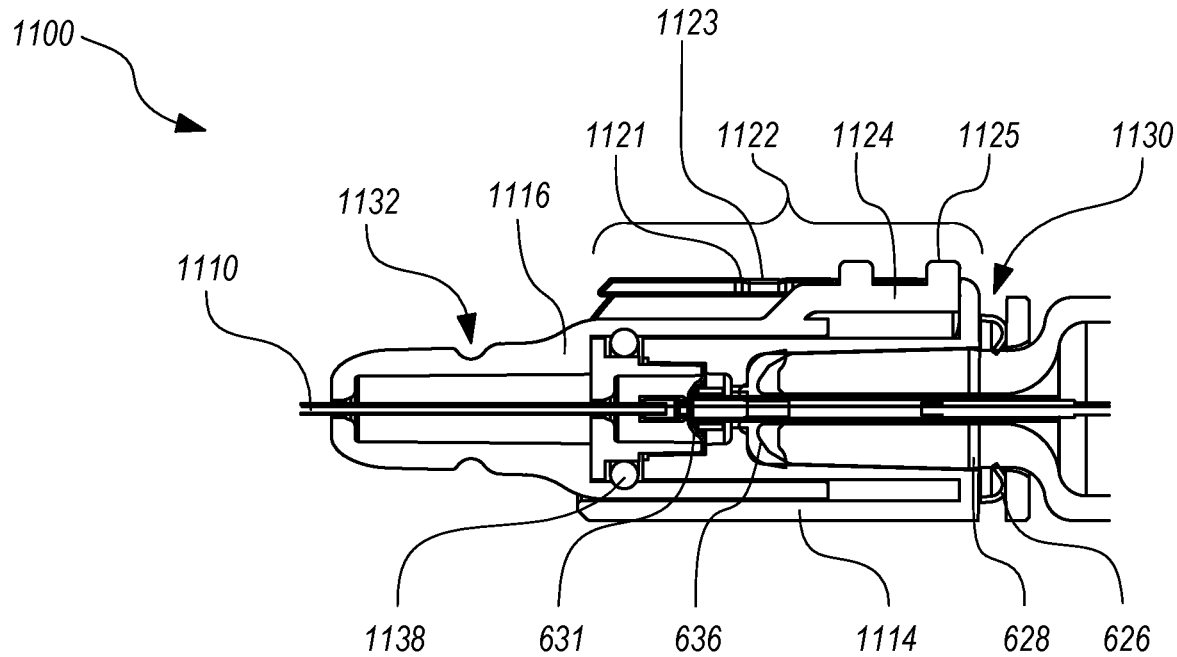
Figure 14B:
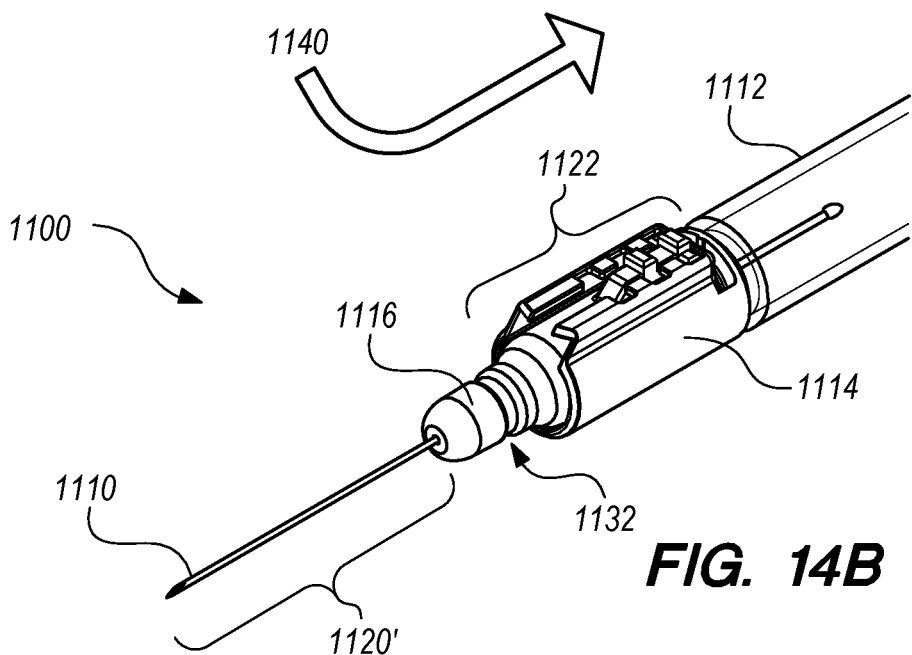

FIGS. 14A and 14B depict the injection system 1100 in a long needle/intramuscular configuration. In the long needle configuration, the two extensions 1125 on the proximal end of pawl 1124 have been moved to their proximal most position relative to the needle hub 1114, thereby placing the actuator 1120 and the needle length spacer 1116 in their respective proximal most positions. This in turn places the injection system 1100 in its long needle/intramuscular configuration in which the exposed length 1120' of the needle 1110 is increased because the needle length spacer 1116 overlaps with less of the needle 1110. The pawl 1124 can be depressed by pushing down on the extensions 1125 to remove the interference and allow the pawl 1124 to move proximally (or distally) relative to the needle hub 1114 along the longitudinal axis of the injection system 1100. This allows the needle length spacer 1116 to move relative to the needle hub 1114 along the longitudinal axis of the injection system 1100 as shown in arrow 1140.

Figure 15:
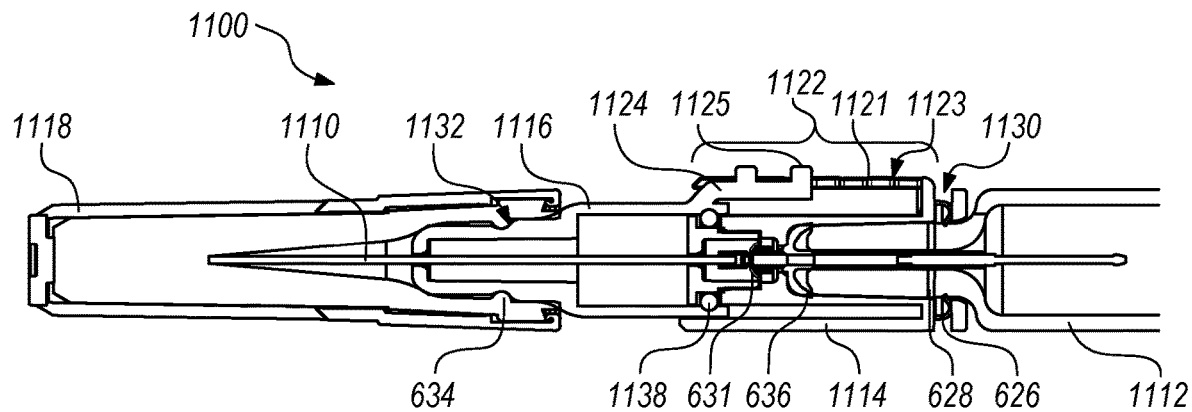

FIG. 15 depicts a preassembled injection system 1100 according to some embodiments. The injection system 1100 includes a needle 1110, a system body 1112, a needle hub 1114, a needle length spacer 1116, and a rigid needle shield 1118. The needle hub 1114 is coupled to the system body 1112 via an interference fit between the retaining ring 626 in the needle hub 1114 and an annular ledge 628 on the system body 1112. The injection system 1100 also includes a movable needle length spacer 1116 which is movably coupled to the needle hub 1114 via an interference fit between extensions 1125 on a pawl 1124 coupled to the needle length spacer 1116 and ratchet teeth 1121 on the needle hub 1114. The needle 1110 is removably coupled to the needle hub 1114 via a pair of needle latches 631 as described in U.S. Utility patent application Ser. No. 14/696,342, which has been previously incorporated by reference herein. The injection system 1100 also includes a rigid needle shield 1118 removably coupled to the needle length spacer 1116. Moreover, the injection system 1100 includes an actuator 1122 configured to move the needle length spacer 1116 along the longitudinal axis of the injection system 1100 thereby modifying/adjusting an exposed length 1120 of the needle 1110.

The injection system 1100 also includes a gasket 636 disposed between the distal end of the system body 1112 and an inner surface of the needle hub 1114. The gasket is configured to prevent contamination of the interior of the system body 1112 and the injectable contained therein. The injection system 1100 further includes an O-ring 1138 disposed between a distal end of the needle hub 1114 and an inner surface of the needle length spacer 1116. The O-ring 1138, in conjunction with the rigid needle shield 1118 (which seals the distal end of the movable needle length spacer 1116 and the needle 1110 tip), are configured to prevent contamination of respective interiors of the needle length spacer 1116 and the needle hub 1114.

By allowing a user to select between short and long needle configurations either before or after removal of the rigid needle shield 1118, the preassembled injection system 1100 described above facilitates use of a single preassembled injection system for both subcutaneous (short needle configuration) and intramuscular (long needle configuration) injections. The preassembled injection system 1100 allows modification of the amount of overlap between the needle length spacer 1116 and the needle 1110 by manual manipulation of an actuator 1122. Selection of a short or long needle configuration from the shipping configuration minimizes the risk of inadvertent needle sticks. Further, the preassembled injection system 1100 allows a user to transition between short and long needle configurations after removal of the rigid needle shield 1118 without exposing fingers to the sharp distal end of the needle 1110 in case the wrong configuration is selected when removing the rigid needle shield 1118. Moreover, the preassembled injection system 1100 minimizes the risk of inadvertent bending the needle 1110 during needle length adjustment, as with the systems that involve manipulation of components near the tip of the needle 1110.

While the preassembled injection system 1100 described above may be selectable between a 0.5 inches short configuration and a 1 inch long configuration, other embodiments include components of different sizes that can result in two configurations with different lengths. While the preassembled injection system 1100 described above includes a luer taper connector, other types of connectors may be used to couple the needle hub to the injection system body. While the preassembled injection system 1100 described above includes the needle latches 631 of a safe injection system, other embodiments may include a standard needle hub assemblies without needle retraction features. While the injection system 1100 is shown in two configurations in FIGS. 13A to 14B, injection systems according to other embodiments may have more than two configurations allowing more than two exposed needle lengths to be manually controlled by the user.

Rotatable Needle Length Spacer

Figure 16:
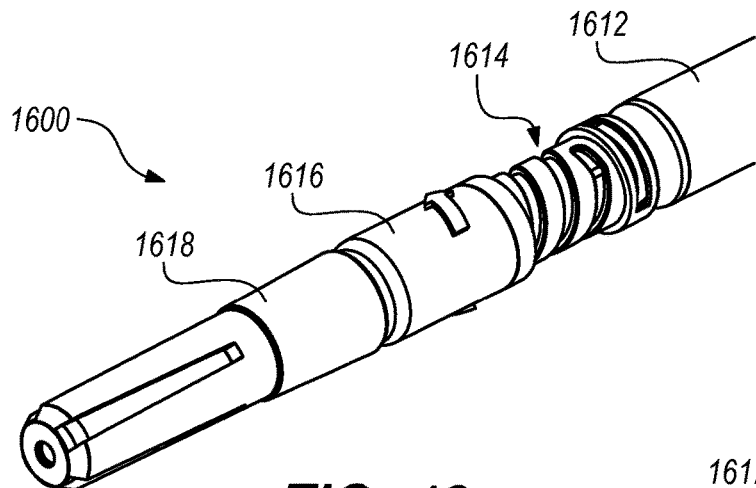
FIGS. 16 to 23 illustrate various aspects of an adjustable/selectable injection system according to some embodiments.
Figure 17:
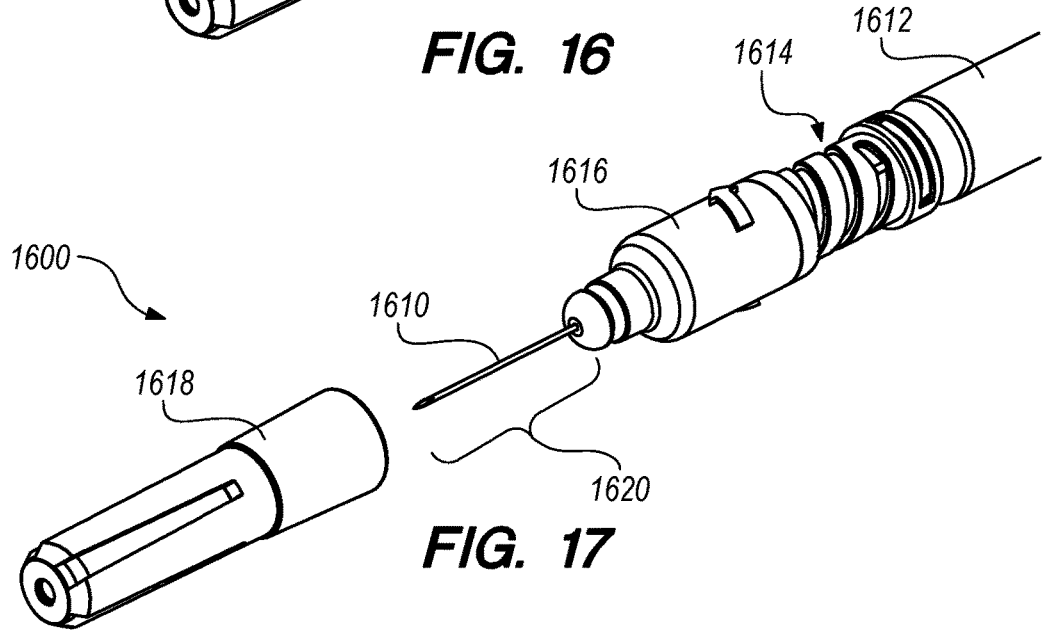
Figure 18:
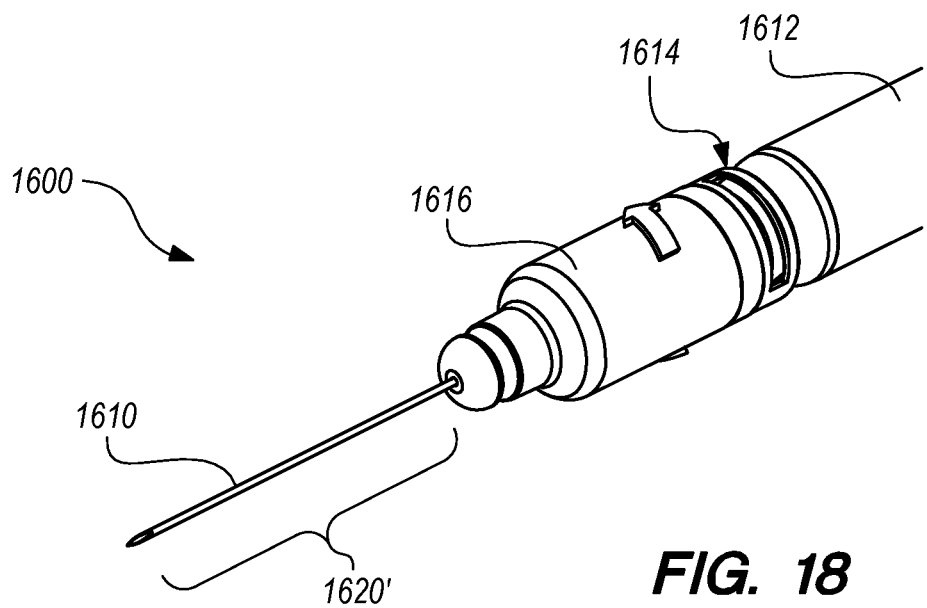

FIGS. 16 to 18 depict a preassembled injection system 1600 including a single needle 1610 with multiple exposed length configurations according to some embodiments. The injection system 1600 includes an injection system body 1612, which may be, for example, a syringe body or a cartridge. The injection system 1600 may be a traditional injection system or a safe injection system that retracts the needle at least partially inside the needle hub 1614 and/or injection system body 1612 after injection to reduce the risk of unintentional needle sticks. Examples of safe injection systems are described in U.S. Utility patent application Ser. No. 14/696,342, which has been previously incorporated by reference herein.

Other components of the injection system 1600, such as stopper members and a plunger rod, are not depicted or described in this specification because the components of the adjustable/selectable exposed needle length injection systems described herein are located at the distal end of the injection systems. The components of the adjustable/selectable exposed needle length injection systems described herein are usable/compatible with off the shelf injection system components such as injection system bodies, stopper members, and plunger rods. The components of the adjustable/selectable exposed needle length injection systems described herein are also usable/compatible with components configured to be compatible with off the shelf injection system components, such as those described in U.S. Utility patent application Ser. No. 14/696,342, which has been previously incorporated by reference herein.

Still referring to FIGS. 16 to 18, the injection system 1600 also includes a movable needle length spacer 1616 which is movably coupled to the needle hub 1614. The needle 1610 is coupled (removably in some embodiments) to the needle hub 1614 through which the needle 1610 extends. The injection system 1600 also includes a rigid needle shield 1618 removably coupled to the needle length spacer 1616 (FIG. 16). The needle hub 1614, the needle length spacer 1616, and features thereof are configured to move the needle length spacer 1616 along the longitudinal axis of the injection system 1600 with rotation of the needle length spacer 1616 relative to the needle hub 1614, thereby modifying/adjusting an exposed length 1620 of the needle 1610 (compare FIGS. 17 and 18). Further details regarding various components of the needle hub 1614 and the needle length spacer 1616 are described below.

FIG. 16 depicts the injection system 1600 with the rigid needle shield 1618 coupled to the needle length spacer 1616. FIG. 17 depicts the injection system 1600 with the rigid needle shield 1618 removed. Removing the rigid needle shield 1618 exposes the sharp distal end of the needle 1610. The injection system 1600 depicted in FIG. 17 is in a short needle/subcutaneous configuration, in which the needle length spacer 1616 is at a distal most position on the needle hub 1614, thereby covering a larger proximal portion of the needle 1610. The exposed length 1620 of the needle 1610 in the short configuration, which extends distally beyond the distal end of the needle length spacer 1616, may be configured to be suitable for subcutaneous injection (e.g., approximately 0.625 inches). FIG. 18 depicts an injection system 1600 in a long needle/intramuscular configuration, in which the needle length spacer 1616 is at a proximal most position on the needle hub 1614, thereby covering a smaller proximal portion of the needle 1610. The exposed length 1620' of the needle 1610 in the long configuration, which extends distally beyond the distal end of the needle length spacer 1616, may be configured to be suitable for intramuscular injection (e.g., approximately 1 inch).

Figure 19:
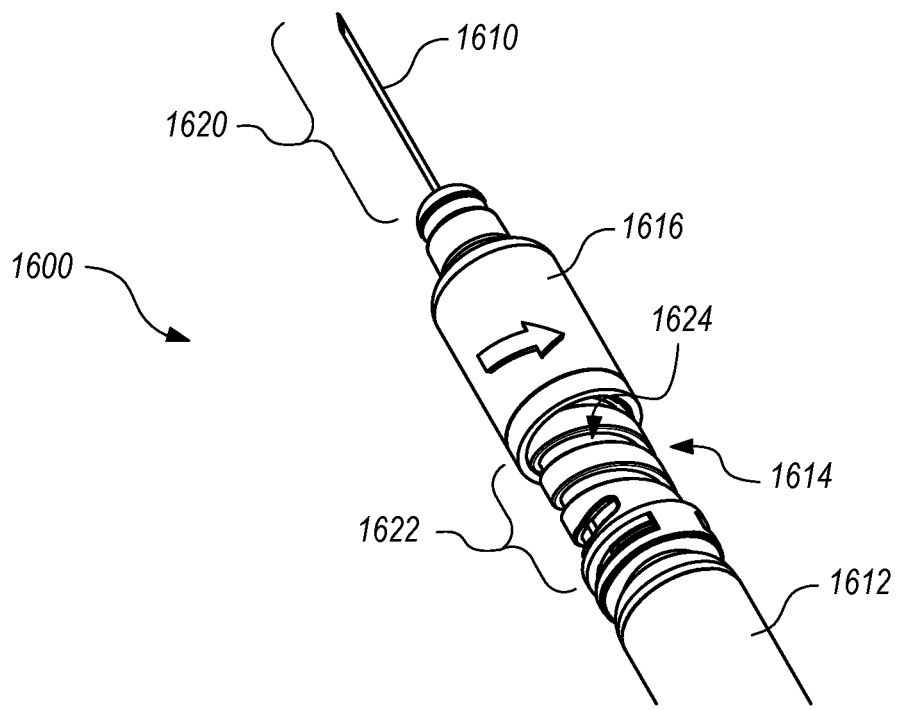

FIG. 19 depicts an injection system 1600 in the short needle/subcutaneous configuration with the rigid needle shield 1618 removed, similar to the injection system 1600 shown in FIG. 17. The needle hub 1614 includes a grooved portion 1622 on which the needle length spacer 1616 is coaxially disposed. The grooved portion 1622 of the needle hub 1614 defines a helical groove. 1624.

Figure 20:
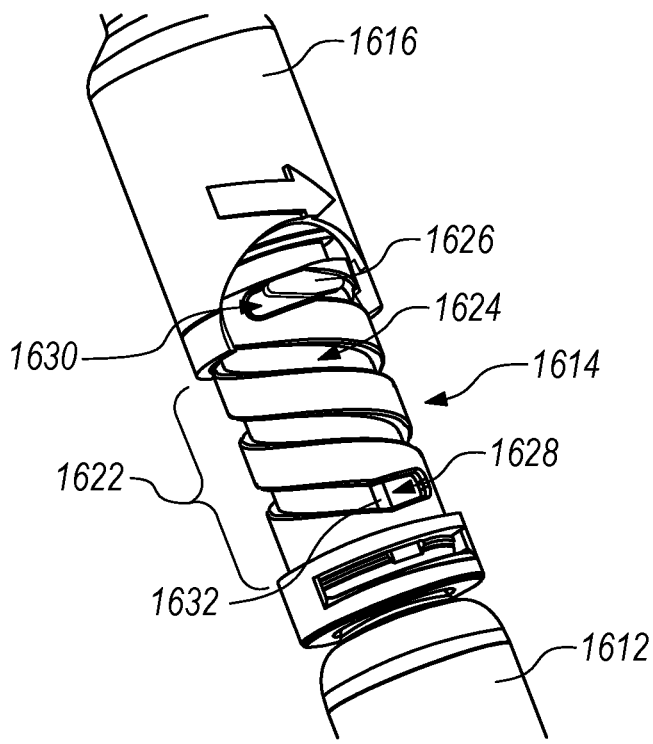

FIG. 20 is a detailed view depicting the distal end of the injection system 1600 in FIG. 19 with a portion of the proximal end of the needle length spacer 1616 cut away to visualize a radially inwardly extending member/wing 1626. The radially inwardly extending member/wing 1626 is part of and extends radially inward from an interior surface of the needle length spacer 1616. The portion of the interior surface of the needle length spacer 1616 from which the radially inwardly extending member/wing 1626 extends has been cut away in FIG. 20 to visualize the radially inwardly extending member/wing 1626.

As shown in FIG. 20, the radially inwardly extending member/wing 1626 extending from the needle length spacer 1616 is disposed in the helical groove 1624 defined by the needle hub 1614. The radially inwardly extending member/wing 1626 is aligned with the middle portion of the helical groove 1624 such that the radially inwardly extending member/wing 1626 can travel in the helical groove 1624 with rotation of the needle length spacer 1616 relative to the needle hub 1614 without significant resistance.

The helical groove 1624 includes flattened proximal and distal ends 1628, 1630, which are circumferential instead of helical due to a change in the slopes of the flattened proximal and distal ends 1628, 1630 relative to the remaining middle portion of the helical groove 1624. As such, the flattened proximal and distal ends 1628, 1630 are skewed relative to/out of alignment with the radially inwardly extending member/wing 1626. The misalignment between the flattened proximal and distal ends 1628, 1630 and the radially inwardly extending member/wing 1626 increases frictional forces therebetween to wedge/retain the radially inwardly extending member/wing 1626 in the flattened proximal and distal ends 1628, 1630. For instance, FIG. 20 shows the radially inwardly extending member/wing 1626 retained in the flattened distal end 1630 of the helical groove 1624, which places the injection system 1600 depicted in the short needle/subcutaneous configuration.

Figure 21:
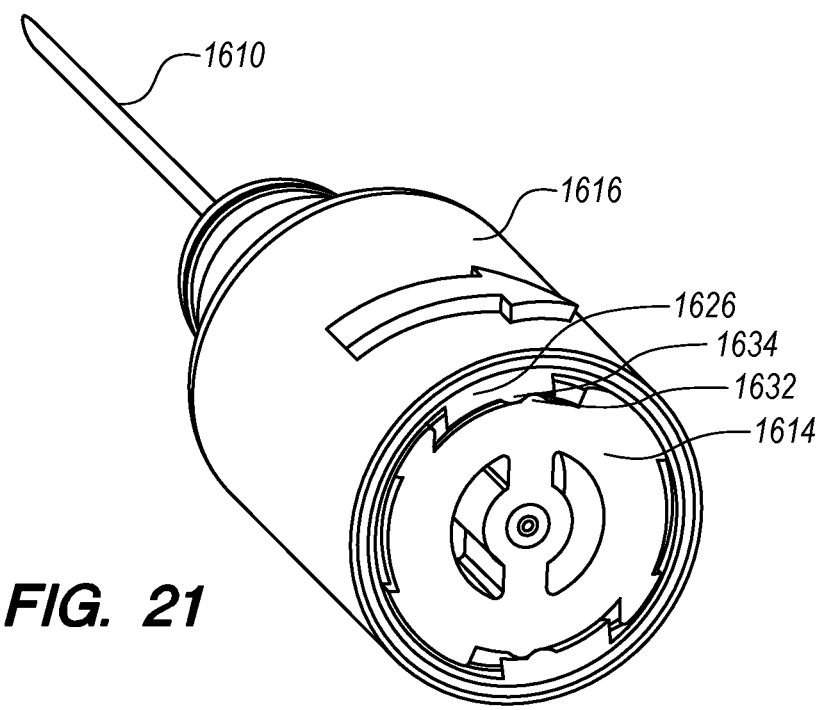

The flattened proximal and distal ends 1628, 1630 of the helical groove 1624 also each include a radially outwardly extending detent 1632 (e.g., 1132 in FIGS. 12-15). The radially outwardly extending detent 1632 is configured to interfere with a radially inwardly extending bump 1634 (FIG. 21) extending radially inward from the radially inwardly extending member/wing 1626 to further retain the radially inwardly extending member/wing 1626 in the flattened proximal and distal ends 1628, 1630. FIG. 21 is a detailed axial cross sectional view of the distal end of the injection system 1600 in FIG. 20. The interference between the radially outwardly extending detent 1632 and the radially inwardly extending bump 1634 increases the force required to remove the radially inwardly extending member/wing 1626 from the flattened proximal and distal ends 1628, 1630 to retain the radially inwardly extending member/wing 1626 in the flattened proximal and distal ends 1628, 1630. While only the proximal end 1628 of the helical groove 1624 is shown with a radially outwardly extending detent 1632, the distal end 1630 of the helical groove 1624 also includes a radially outwardly extending detent 1632.

Figure 22:
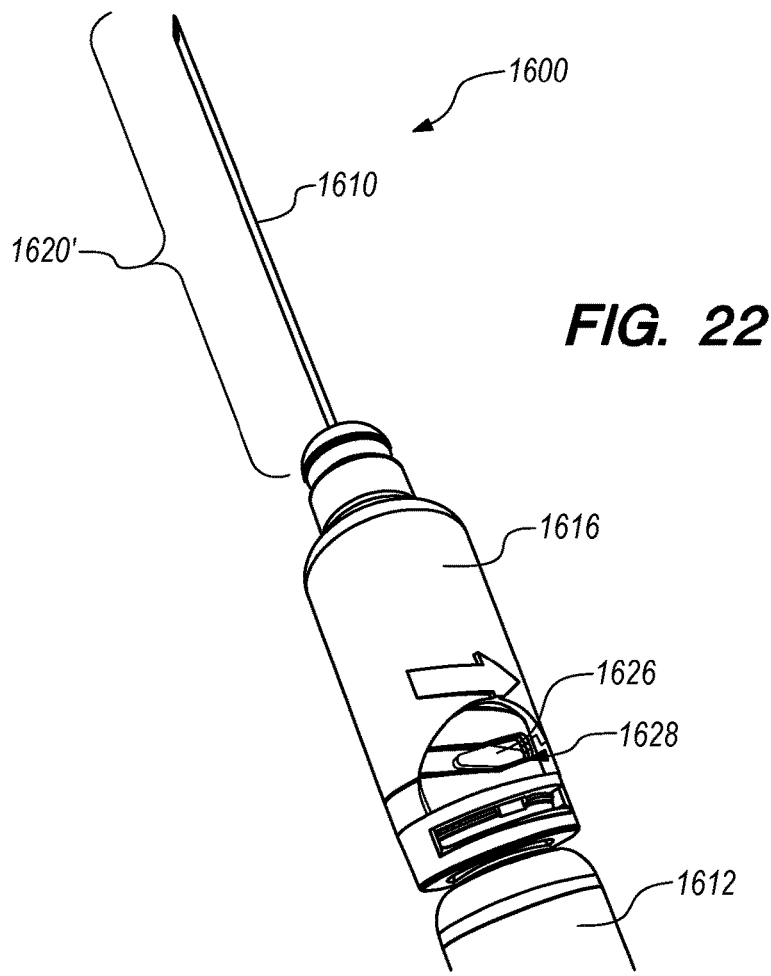

FIG. 22 shows the radially inwardly extending member/wing 1626 retained in the flattened proximal end 1628 of the helical groove 1624, which places the injection system 1600 depicted in the long needle/intramuscular configuration. This configuration is similar to one shown in FIG. 18 and described above.

Figure 23:
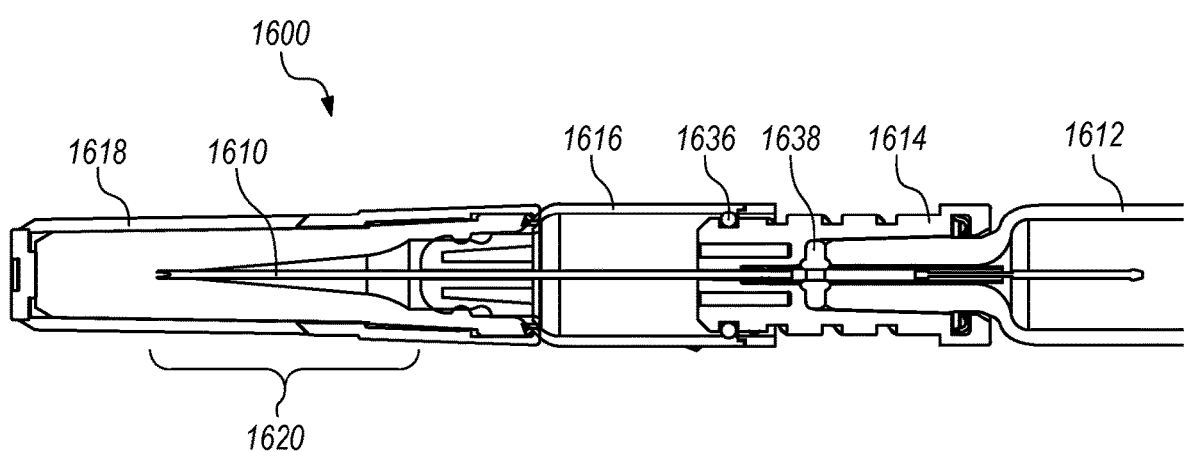

FIG. 23 is a longitudinal cross sectional view of a distal end of an injection system 1600 according to some embodiments. The injection system 1600 is similar to the injection system 1600 depicted in FIG. 16 where the injection system 1600 is in short needle/subcutaneous configuration with the rigid needle shield 1618 coupled thereto. The configuration depicted in FIG. 23 is the transport configuration in which the preassembled injection system 1600 is shipped. In this configuration, the rigid needle shield 1618 seals the distal tip of the needle 1610 and the exposed length 1620 thereof against contamination from the environment. The injection system 1600 also includes an O-ring 1636 disposed between the needle hub 1614 and the needle length spacer 1616 to seal against (e.g., particulate) contamination from the environment. The injection system 1600 further includes a gasket 1638 disposed between the injection system body 1612 and the needle hub 1614 and around a proximal potion of the needle 1610 to seal against (e.g., particulate) contamination from the environment.

From the transport configuration depicted in FIGS. 16 and 23, a user can remove the rigid needle shield 1618 from the injection system 1600 to prepare the injection system 1600 for use as shown in FIGS. 17 and 19. In FIGS. 17 and 19, the injection system 1600 is in the short needle/subcutaneous configuration. In order to convert the injection system 1600 to the long needle/intramuscular configuration depicted in FIGS. 18 and 22, the user can rotate the needle length spacer 1616 relative to the needle hub 1614 in the direction indicated on the needle length spacer 1616 to move the needle length spacer 1616 from a distal position to a proximal position. The direction of rotation is dictated by the direction of the helical groove, which may be modified to modify the direction of rotation. In some embodiments, 1.5 rotations of the needle length spacer 1616 relative to the needle hub 1614 moves the needle length spacer 1616 from a distal position to a proximal position.

By allowing a user to select between short and long needle configurations, the preassembled injection system 1600 described above facilitates use of a single preassembled injection system for both subcutaneous (short needle configuration) and intramuscular (long needle configuration) injections. The preassembled injection system 1600 allows a user to transition between short and long needle configurations after removal of the rigid needle shield 1618 without exposing fingers to the sharp distal end of the needle 1610 in case the wrong configuration is selected when removing the rigid needle shield 1618. Moreover, the preassembled injection system 1600 minimizes the risk of inadvertent bending the needle 1610 during needle length adjustment, as with the systems that involve manipulation of components near the tip of the needle 1610. Coaxial placement of the needle length spacer 1616 around the needle 1610 also minimizes the risk of inadvertent bending the needle 1610.

Figure 24:
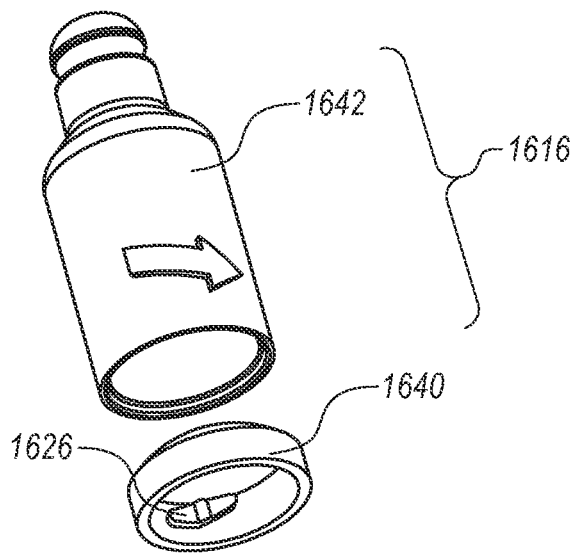
FIGS. 24 and 25 illustrate various aspects of a method of manufacturing an injection system according to some embodiments.
Figure 25:
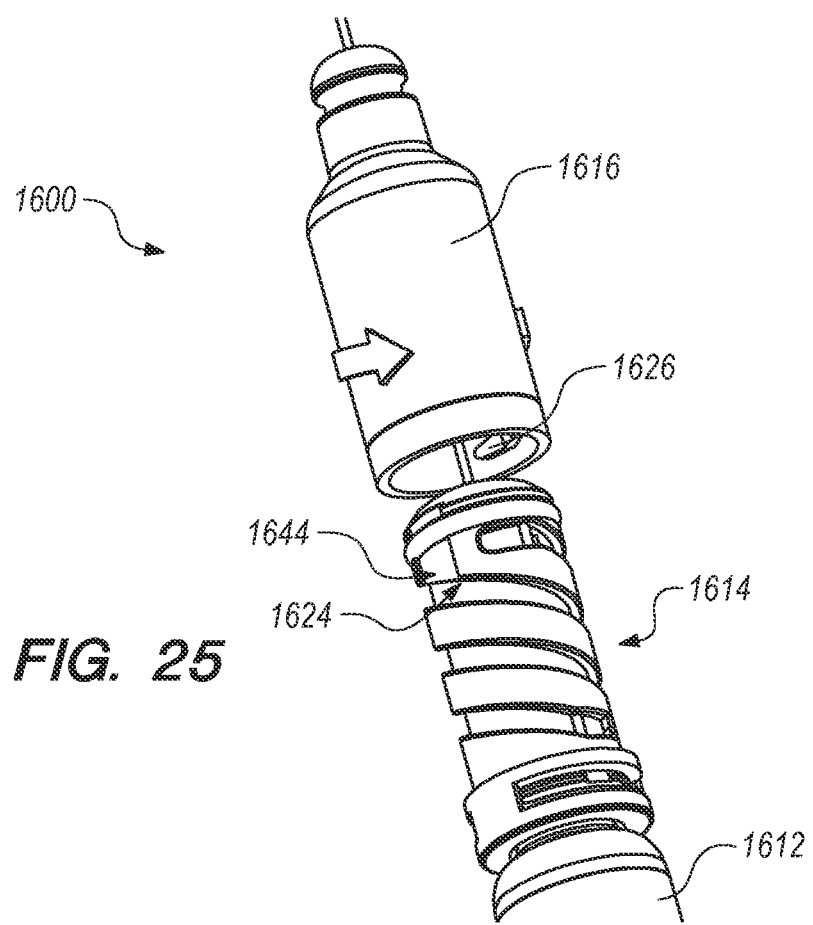

FIGS. 24 and 25 depict the manufacturing of injection systems 1600 like those depicted in FIGS. 16 to 23 according to some embodiments. FIG. 24 depicts a threaded collar 1640, which can be bonded to a distal portion 1642 to form the needle length spacer 1616. The radially inwardly extending member/wing 1626 can be formed in the threaded collar 1640 before the threaded collar 1640 is bonded to the distal portion 1642. These two components can be bonded ultrasonically or by laser welding.

FIG. 25 depicts positioning of the needle length spacer 1616 and the needle hub 1614 to allow the needle length spacer 1616 to be snapped over a distal end of the needle hub 1614. The needle hub 1614 includes a longitudinal groove 1644 to facilitate the snapping the needle length spacer 1616 over the needle hub 1614 to position the radially inwardly extending member/wing 1626 into the helical groove 1624.

While the injection systems 1600 depicted in FIGS. 16 to 23 only illustrate one helical groove 1624, injection systems according to some embodiments include a plurality of helical grooves with a corresponding plurality of radially inwardly extending members/wings. Injection systems including respective pluralities of helical grooves and radially inwardly extending members/wings may distribute loads/forces during use more evenly. While the injection systems 1600 depicted in FIGS. 16 to 23 include only flattened proximal and distal ends 1628, 1630 and corresponding radially outwardly extending detents 1632, injection systems according to some embodiments include one or more flattened sections and corresponding radially outwardly extending detents in the middle section of the helical groove to provide additional stopping points during longitudinal movement of the needle length spacer. These additional stopping points in turn provide corresponding additional needle length options for the injection systems.

While the preassembled injection system 1600 described above may be selectable between a 0.625 inches short configuration and a 1 inch long configuration, other embodiments include components of different sizes that can result in two configurations with different lengths. While the preassembled injection system 1600 described above includes a luer taper connector, other types of connectors may be used to couple the needle hub to the injection system body. While the preassembled injection system 1600 described above includes a standard needle hub assembly without needle retraction features, other embodiments may include needle latches of safe injection systems.

While the various systems and methods described herein depict injection systems having manually actuated plunger members, the needle length adjustment systems and methods described herein work equally well with automated or semi-automated injection systems such as injection pens.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject injection information collection procedures may be provided in packaged combination for use in executing such interventions. These supply "kits" may further include instructions for use and/or may be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. An injection system, comprising:
    a body member having a body connection member at a distal end thereof; and
    a needle hub assembly coupled to the distal end of the injection system body, the needle hub assembly comprising
        a needle hub coupled to the body connection member, the needle hub comprising a raised structure having a flattened surface,
        a needle coupled to the needle hub, and
        a spacer movably coupled to the needle hub;
    an actuator configured to move the spacer along a longitudinal axis of the injection system,
    wherein moving the spacer along the longitudinal axis modifies an exposed length of the needle, and
    wherein the actuator comprises
        a plurality of ratchet teeth on the flattened surface on the raised structure of the needle hub defining a plurality of discrete spaces, and
        a pawl coupled to the spacer, wherein the pawl is configured to movably lodge in each of the plurality of discrete spaces,
    wherein moving the pawl along the longitudinal axis moves the spacer along the longitudinal axis,
    wherein pushing the pawl radially inward releases the spacer to move proximally or distally between the plurality of discrete spaces,
    wherein the pawl is biased to move radially outward such that the spacer is prevented from moving between the plurality of discrete spaces,
    wherein moving the pawl from a distal most position to a proximal most position changes the system from a first exposed needle length to a second exposed needle length, and
    wherein the first exposed needle length is shorter than the second exposed needle length.

2. The system of claim 1, further comprising a gasket disposed between the distal end of the body member and an inner surface of the needle hub.

3. The system of claim 2, wherein the gasket is configured to prevent contamination of an interior of the body member.

4. The system of claim 1, further comprising an O-ring disposed between a distal end of the needle hub and an inner surface of the spacer.

5. The system of claim 4, wherein the O-ring is configured to prevent contamination of an interior of the spacer.

6. The system of claim 1, wherein the plurality of ratchet teeth comprises a plurality of pairs of opposing ratchet teeth on the flattened surface of the raised structure of the needle hub, defining a plurality of pairs of opposing discrete spaces.

7. The system of claim 6, wherein the pawl comprising a pair of opposing laterally extending pegs configured to interfere with each of the plurality of pairs of opposing discrete spaces to removably position the spacer relatively to the needle hub.

* * * * *